(12) United States Patent
Liu et al.

(10) Patent No.: US 12,600,979 B2
(45) Date of Patent: Apr. 14, 2026

(54) **GENE *bHLH35* FOR PROMOTING ANTHOCYANIN ACCUMULATION OF PLANTS AND APPLICATION THEREOF**

(71) Applicant: Lanzhou University, Lanzhou (CN)

(72) Inventors: Jianquan Liu, Lanzhou (CN); Pan Zhang, Lanzhou (CN); Minjie Li, Lanzhou (CN); Han Zhang, Lanzhou (CN)

(73) Assignee: Lanzhou University, Lanzhou (CN)

( * ) Notice: Subject to any disclaimer, the term of this patent is extended or adjusted under 35 U.S.C. 154(b) by 42 days.

(21) Appl. No.: 18/582,845

(22) Filed: Feb. 21, 2024

(65) Prior Publication Data

US 2025/0207146 A1     Jun. 26, 2025

(30) Foreign Application Priority Data

Dec. 23, 2023   (CN) ......................... 202311784450.X

(51) Int. Cl.
*C12N 15/82*       (2006.01)
*C12Q 1/6895*      (2018.01)

(52) U.S. Cl.
CPC ..... *C12N 15/8271* (2013.01); *C12N 15/8205* (2013.01); *C12Q 1/6895* (2013.01); *C12Q 2600/13* (2013.01); *C12Q 2600/158* (2013.01)

(58) Field of Classification Search
CPC ............ C12N 15/8271; C12N 15/8205; C12Q 1/6895; C12Q 2600/13; C12Q 2600/158
See application file for complete search history.

(56) References Cited

FOREIGN PATENT DOCUMENTS

| CN | 108018290 A | 5/2018 |
| CN | 112126651 A | 12/2020 |
| CN | 116121269 A | 5/2023 |

OTHER PUBLICATIONS

Jiang, L., Tian, X., Li, S., Fu, Y., Xu, J., & Wang, G. (2019). The AabHLH35 transcription factor identified from Anthurium andraeanum is involved in cold and drought tolerance. Plants, 8(7), 216. (Year: 2019).*

Bauer, P., Thiel, T., Klatte, M., Bereczky, Z., Brumbarova, T., Hell, R., & Grosse, I. (2004). Analysis of sequence, map position, and gene expression reveals conserved essential genes for iron uptake in *Arabidopsis* and tomato. Plant Physiology, 136(4), 4169-4183. (Year: 2004).*

NCBI Reference Sequence: NM_001203627.1. *Arabidopsis thaliana* basic helix-loop-helix (bHLH) DNA-binding superfamily protein (AT5G57150), mRNA. Bethesda (MD): National Library of Medicine (US), Ncbi. Oct. 20, 2022. Available from: https://www.ncbi.nlm.nih.gov/nuccore/NM_00120. (Year: 2022).*

(Continued)

*Primary Examiner* — Amjad Abraham
*Assistant Examiner* — Dequantarius Javon Speed

(57)         ABSTRACT

The present invention relates to a method for cultivating transgenic plants having increased anthocyanin content and enhanced tolerance to biotic and abiotic stress environments. The method comprises transferring a bHLH35 gene into recipient plants using a genetic engineering transformation method, to obtain transgenic plants having increased anthocyanin content and tolerance to biotic and abiotic stress environments. The bHLH35 gene may be selected from a ChbHLH35 gene from *Corydalis hemidicentra* or an AtbHLH35 gene from *Arabidopsis thaliana*.

1 Claim, 5 Drawing Sheets

Specification includes a Sequence Listing.

(56)         References Cited

OTHER PUBLICATIONS

Niu, Y., Chen, Z., Stevens, M., & Sun, H. (2017). Divergence in cryptic leaf colour provides local camouflage in an alpine plant. Proceedings of the Royal Society B: Biological Sciences, 284(1864), 20171654. (Year: 2017).*

Zhang YQ, Lu X, Zhao FY, Li QT, Niu SL, Wei W, Zhang WK, Ma B, Chen SY, Zhang JS. Soybean GmDREBL Increases Lipid Content in Seeds of Transgenic *Arabidopsis*. Sci Rep. Oct. 3, 2016;6:34307. doi: 10.1038/srep34307. PMID: 27694917; PMCID: PMC5046110. (Year: 2016).*

* cited by examiner

**Subdivision by *A. thaliana* (Group III)**

GENE *bHLH35* FOR PROMOTING ANTHOCYANIN ACCUMULATION OF PLANTS AND APPLICATION THEREOF

CROSS-REFERENCE TO RELATED APPLICATIONS

The application claims priority to Chinese patent application No. 202311784450X, filed on Dec. 23, 2023, the entire contents of which are incorporated herein by reference.

SEQUENCE LISTING

The sequence listing xml file submitted herewith, named "gene_bHLH35_for_promoting_anthocyanin_accumulation_of_plants_and_application_thereof.xm l", created on Feb. 20, 2024, and having a file size of 6,383 bytes, is incorporated by reference herein.

TECHNICAL FIELD

The present invention relates to the field of biotechnology, and in particular to a bHLH35 gene for promoting anthocyanin accumulation of plants and an application thereof.

BACKGROUND

Anthocyanins are important secondary metabolites widely distributed in plants. They are mainly stored in vacuoles of plant cells in a water-soluble form and contribute to the diverse colors exhibited by plants (Li et al., 2022). China has long utilized anthocyanins, which are pigments that can be used in food. With in-depth study of anthocyanin, it has been found that anthocyanin played a significant role in the growth development progress and stress response in plants. For example, anthocyanins help plants respond to biotic stressors like pest and disease resistance, help plants form their color in flowers and fruits, and attracted insects and birds that dispersed pollen and seeds. Anthocyanins have strong oxidation resistance and have been widely used in food and medical industries in recent years. Examples of these applications include the prevention and adjuvant treatment of cardiovascular, cerebrovascular disorders, the enhancement of blood sugar regulation and the treatment of cancer. (Butelli et al., 2008: Sun et al., 2013; Kaur et al., 2023: Alappat and Alappat, 2020).

*Corydalis hemidicentra* is a perennial herb plant, and mainly distributed in the Hengduan Mountains' alpine screes. Its habitat features high altitude, strong UV radiation, an annual average temperature below −4° C. and a large temperature difference between day and night. The oligophagous Parnassius butterflies in this region mostly rely on vision to locate *Corydalis* plants and lay their eggs on rocks near them to ensure the hatched larvae feed on *Corydalis* leaves (Niu et al., 2014). In order to adapt to an extremely harsh environment and avoid the oviposition of the natural enemy Parnassius butterflies, some *Corydalis* populations have evolved rich color variations. Such as the color variation of *Corydalis hemidicentra* ranges from whitish grey to reddish grey or dark grey, making it resemble the color of gravel in a growing place. Differences in composition and concentration of anthocyanin and chlorophyll in leaf epidermal cells of *Corydalis hemidicentra* constitute a physiological and biochemical basis of its leaf color variation (Niu et al., 2017). Because the anthocyanin content of the camouflaged grey leaves is significantly higher than the chlorophyll content, individuals in the population are better able to hide themselves and withstand harsh weather conditions.

Transcription factors are a class of proteins that bind to specific sequences in their target genes and regulate the transcription levels of the genes. Basic/helix-loop-helix (bHLH) transcription factors are distributed in different plant species and are the second major family of transcription factors in plants. Members of bHLH family share two conserved domain databases of about 60 amino acids: a basic region (b) involved in DNA binding, which can specifically recognize the regulatory element E-box (CANNTG) or G-Box (CACGTG) of target genes, and two hydrophobic α-helix and amino acid loop domains (HLH) which can form homodimers or heterodimers. They are divided into 12 distinct subfamilies in *Arabidopsis thaliana*, which are bHLH I to bHLH XII (Hao et al., 2021). Members of bHLH family are widely involved in the processes of plant growth and development and stress responses. For example, BR ENHANCED EXPRESSION 1 (BEE1, bHLH44) can be stabilized by blue light to systematically control a photoperiod-mediated plant flowering process. (Wang et al., 2019); AtbHLH57 and ODR1 (a seed dormancy-related protein) can combine to suppress the transcription of NCED, which is an enzyme gene involved in ABA biosynthesis, by lowering endogenous ABA content to relieve seed dormancy (Liu et al., 2020); the heterologous expression of PebHLH35 from *Populus euphratica* in *Arabidopsis thaliana* has been shown to effectively decrease the stomatal density and opening in the leaves, leading to a reduction in transpiration rate. This modulation ultimately enhances the drought resistance of transgenic *Arabidopsis thaliana* plants (Dong et al., 2014); a bHLH transcription factor ICE1 performs transcriptional activation on the expression of CBFs at an early stage of chilling injury, then activating the expression of a downstream antifreeze gene and enhancing the freezing resistance of plants (Lee et al., 2005). In response to external stress, plants usually synthesize some specialized metabolites to improve their resistance, and one such secondary metabolites is anthocyanin. The anthocyanin biosynthesis in plants is mainly regulated by MYB-bHLH-WDR (MBW) ternary complex (Xu et al., 2015), for example, by overexpression of R2R3-MYB transcription factor GhPAPID in cotton. This overexpression resulted in an elevation of anthocyanin content, particularly under light induction. As a result, the resistance of transgenic cotton plants to cotton bollworms and spider mites was significantly enhanced (Li et al., 2019); a tomato bHILH transcription factor SlJAF13 promotes the accumulation of anthocyanin in fruit by activating the expression of SlAN1 in the MBW complex (Chen et al., 2022); the bHLH gene displays negative regulation in addition to activating genes involved in downstream anthocyanin biosynthesis, such as overexpressing of CpbHLH1 gene from *Chimonanthus praecox* (L.) in *Arabidopsis thaliana* results in a reduction in anthocyanin accumulation (Zhao et al., 2020).

The inventor of this application found a highly expressed ChbHLH35 gene from its grey population when researched on the color variation of *Corydalis hemidicentra*, and the orthologous gene AtbHLH35 also found in *Arabidopsis thaliana* with a distant genetic relationship. The related function of bHLH35 in regulating anthocyanin biosynthesis in *Arabidopsis thaliana* or any other plants has not been reported. Experiments have found that overexpression of bHLH35 in *Arabidopsis thaliana* and *Lactuca sativa* var. *ramosa* Hort. can significantly increase the anthocyanin content. The inventor of this application has created multiple plants with high anthocyanin content by overexpressing two orthologous genes, bHLH35 from *Corydalis hemidicentra* and *Arabidopsis thaliana*. These genes hold great potential for utilization in crop breeding aimed at enhancing insect resistance, antioxidation and promoting health benefits related to aging.

SUMMARY

A purpose of the present invention is to solve the above problems in the prior art and provides the bHLH35 gene for promoting anthocyanin accumulation of plants and an application thereof. To achieve the above purpose, a technical solution of the present invention is as follows:

The present invention provides bHLH35 for promoting anthocyanin accumulation of plants. The bHLH35 genes are from *Corydalis hemidicentra* (ChbHLH35), *Arabidopsis thaliana* (AtbHLH35) or orthologous genes from other angiosperms (the gene sequence similarity is between ChbHLH35 and AtbHLH35, or similar to the two genes; the sequence difference is within 5 percent); a nucleotide sequence of *Corydalis hemidicentra* ChbHLH35 gene is shown in SEQ ID No: 1; an amino acid sequence of *Corydalis hemidicentra* ChbHLH35 gene is shown in SEQ ID No: 2; a nucleotide sequence of *Arabidopsis thaliana* AtbHLH35 gene is shown in SEQ ID No: 3; an amino acid sequence of *Arabidopsis thaliana* AtbHLH35 gene is shown in SEQ ID No: 4.

Further, the plants are angiosperms.

The present invention also provides an application of the bHLH35 gene for promoting anthocyanin accumulation of plants in breeding of transgenic plants with high anthocyanin content.

The present invention also provides an application of the bHLH35 gene for promoting anthocyanin accumulation of plants in breeding of transgenic plants with tolerance to an abiotic stress environment.

The present invention also provides an application of the bHLH35 gene for promoting anthocyanin accumulation of plants in breeding of transgenic plants with tolerance to a biotic stress environment.

The present invention also provides a method for cultivating transgenic plants with high anthocyanin content and tolerance to biotic and abiotic stress environments, comprising the following step:

transferring the bHLH35 gene mentioned above into plants by means of genetic engineering to obtain transgenic plants with high anthocyanin content and tolerance to biotic and abiotic stress environments.

The following sequences are involved in the solution of the present invention:

the nucleotide sequence of *Corydalis hemidicentra* ChbHLH35 (CheG0011994.1) gene_
                                    SEQ ID No: 1
ATGGAACACATTGATGAAGACTACAAACATTACTGGGAAACAAAA

ATGTTTTTTCAAAATGAAGAACTCGACAGTTTGGTTTACGACGAG

CAAATTTCCGGTTACGACGAGCAAGTTTCGGGTTACTATGATTCG

AGCTCTCCGGACGCTTCATCGGTCACAGCGAAAAATATAATTTCA

GAAAGAAATAGGAGGAAAAAACTTAATGATAGATTATTTGCATTA

AGAGCTGTGGTTCCTAATATTAGCAAGATGGATAAAGCATCGATA

ATTAAGGACGCGATCGAGTACATCCAAGAATTACACGAACAAGAA

-continued
CGAGCAATCCAAGTAGAGTTAATTGAGCTCGAATCGGGGAAATTG

AAGAAACCCATGTTGGATATCGAACGACAAAATGCAGGTTTATTG

AAGACGAAGAAAAAGAGAATAGATACTAATTATGATTCGAGTGGA

TCGAGATCGTCATCGATCGAATTGCTAGAGCTTAGAGTTTCGTAC

GTGGGAGATAGAACTATGGTGGTAAGTCTCACGTGCGATAAAAAA

ACAGACACAATGGTGAAGCTCTGTGAAGTTTTCGAGTCTTTGAAG

CTTAAAATAGTCACTGCAAGTATCACTGTTTTCTCAGGGAGACTT

CTCAAGACTGTCTTTGTCGAGGTAATTTACTAA.

the amino acid sequence of *Corydalis hemidicentra* ChbHLH35 (CheG0011994.1) gene_
                                    SEQ ID No: 2
MEHIDEDYKHYWETKMFFQNEELDSLVYDEQISGYDEQVSGYYDS

SSPDASSVTAKNIISERNRRKKLNDRLFALRAVVPNISKMDKASI

IKDAIEYIQELHEQERAIQVELIELESGKLKKPMLDIERQNAGLL

KTKKKRIDTNYDSSGSRSSSIELLELRVSYVGDRTMVVSLTCDKK

TDTMVKLCEVFESLKLKIVTASITVFSGRLLKTVFVEVIY.

the nucleotide sequence of *Arabidopsis thaliana* AtbHLH35 (AT5G57150) gene)_
                                    SEQ ID No: 3
ATGGAGGATATCGTCGACCAAGAATTAAGCAATTACTGGGAACCT

AGCTCCTTCCTCCAAAACGAAGACTTCGAATACGACAGAAGCTGG

CCTTTGGAAGAAGCCATTTCTGGGTCGTATGATTCGAGTTCGCCG

GATGGAGCTGCTTCGTCGCCGGCTTCTAAGAATATTGTGTCGGAG

AGAAACAGAAGACAGAAACTTAACCAGAGACTCTTCGCTCTTCGA

TCAGTTGTTCCCAATATCACTAAGATGGATAAAGCCTCAATAATC

AAAGATGCTATTAGTTACATAGAAGGATTACAATATGAAGAAAG

AAGCTCGAAGCTGAGATCAGAGAACTTGAATCTACACCAAAGAGT

AGCCTTAGTTTCAGCAAAGATTTTGATCGTGATTTACTTGTTCCT

GTCACATCCAAGAAGATGAAGCAGCTTGATTCTGGTTCTTCCACT

TCTCTCATCGAAGTTCTCGAATTGAAGGTAACATTCATGGGAGAG

AGGACAATGGTGGTGAGTGTAACATGTAATAAGAGGACAGATACA

ATGGTGAAACTGTGTGAAGTCTTTGAGTCATTGAATCTCAAAATC

CTCACTTCCAATCTCACCTCTTTCTCTGGCATGATCTTCCACACT

GTCTTTATTGAGTTGCGACCAAACATTTATTGGGTTGTGTGGTTT

TTAGTTTTTATGTCTATTTTTGGTCCCACAATTATTGTAATTTGG

TCCATTTGGTTTATTAAAAAGAAAATAATATTATCTCTGTGGCGG

ATGAAGAAGAACAAGAGGTGTTGCGGTTAA.

the amino acid sequence of *Arabidopsis thaliana* AtbHLH35 (AT5G57150) gene)_
                                    SEQ ID No: 4
MEDIVDQELSNYWEPSSFLQNEDFEYDRSWPLEEAISGSYDSSSP

DGAASSPASKNIVSERNRRQKLNQRLFALRSVVPNITKMDKASII

KDAISYIEGLQYEEKKLEAEIRELESTPKSSLSFSKDFDRDLLVP

VTSKKMKQLDSGSSTSLIEVLELKVTFMGERTMVVSVTCNKRTDT

-continued

MVKLCEVFESLNLKILTSNLTSFSGMIFHTVFIELRPNIYWVVWF

LVFMSIFGPTIIVIWSIWFIKKKIILSLWRMKKNKRCCG.

Compared with the prior art, the solution has the following beneficial effects.

The solution of the present invention provides the bHLH35 gene for promoting anthocyanin accumulation of plants and an application thereof in breeding of transgenic plants. The bHLH35 genes from *Corydalis hemidicentra* (ChbHLH35) and *Arabidopsis thaliana* (AtbHLH35) in the present invention are bHLH transcription factors, are able to promote the accumulation of anthocyanin in plants; Moreover, transgenic *Arabidopsis thaliana* and *Lactuca sativa* var. *ramosa* Hort. with ChbHLH35 and AtbHLH35 obtained through genetic engineering demonstrated elevated anthocyanin accumulation; The discovery and application of bHLH35 genes described in this invention hold significant theoretical and practical implications for the cultivation of agricultural products with enhanced insect resistance, antioxidation, and health benefits related to aging.

DETAILED DESCRIPTION OF THE EMBODIMENTS

Figure 1:
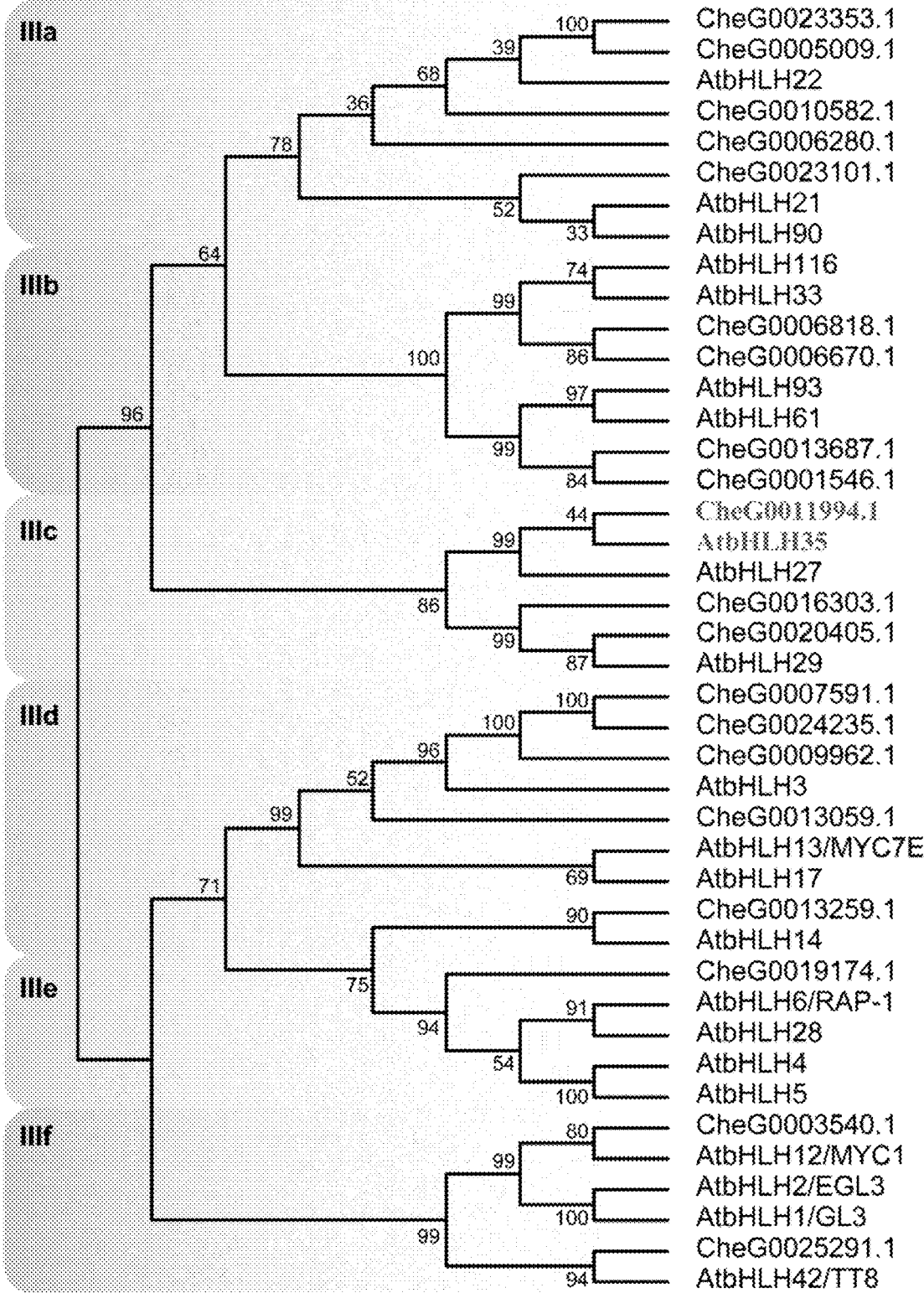
FIG. 1 is a pylogenetic tree of the bHLH families of *Corydalis hemidicentra* and *Arabidopsis thaliana*. *Corydalis hemidicentra* ChbHLH35 (CheG0011994.1) and *Arabidopsis thaliana* AtbHLH35 are orthologous genes (Maximum likelihood tree, bootstrap=1000) in the present invention.
Figure 2:
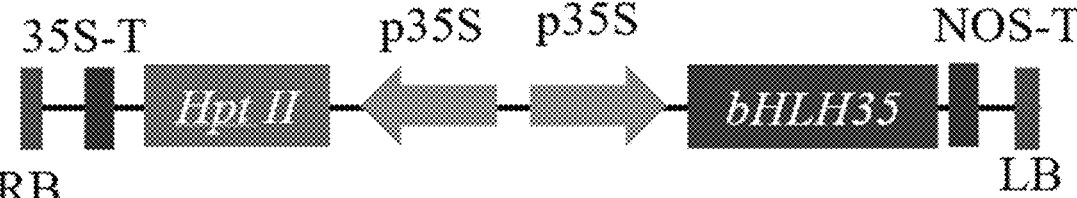
FIG. 2 is a diagram illustrating ChbHLH35 and AtbHLH35 overexpression vectors (where pCAMBIA1300-ChbHLH35 and pCAMBIA3300-AtbHLH35 are used for transgenic *Arabidopsis thaliana*, and pCAMBIA3300-AtbHLH35 is used for transgenic *Lactuca sativa* var. *ramosa* Hort.).
Figure 3:
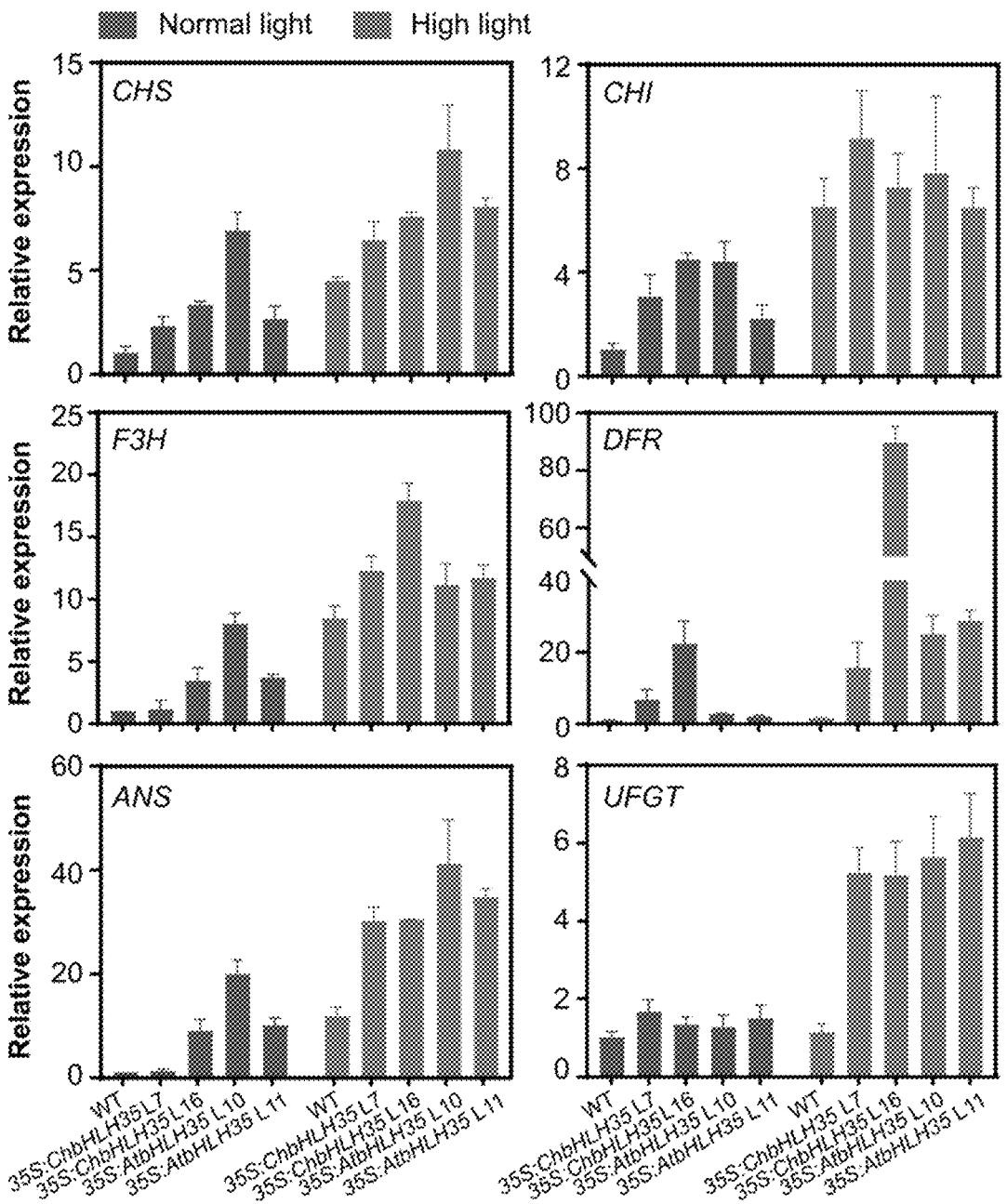
FIG. 3 shows expression of anthocyanin biosynthesis-related genes in transgenic *Arabidopsis thaliana* (overexpressed ChbHLH35 and AtbHLH35 in an embodiment of the present invention).
Figure 4:
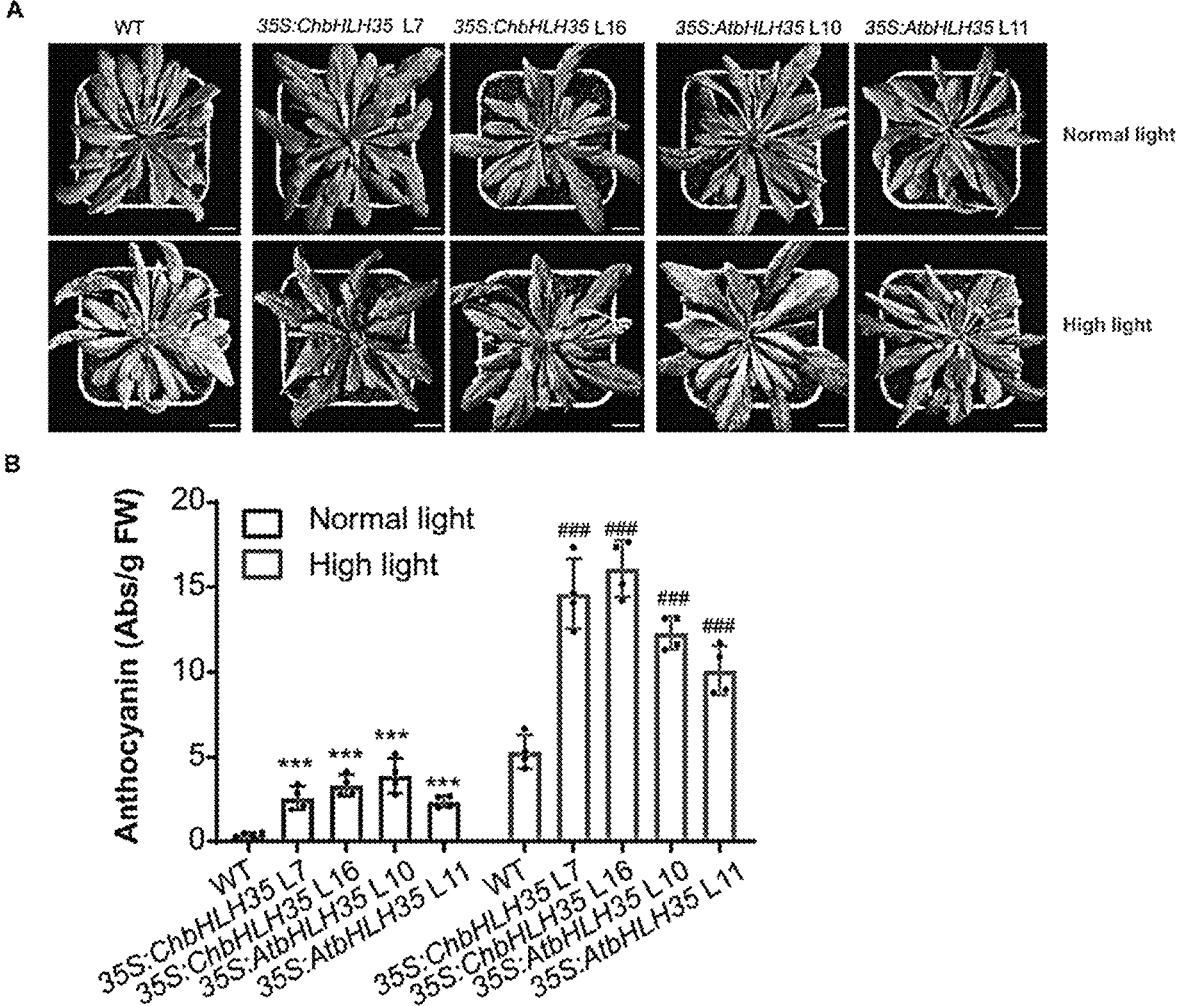
FIG. 4 shows an overexpression phenotype (A) and anthocyanin accumulation content determination (B) of *Arabidopsis thaliana* (overexpressed ChbHLH35 and AtbHLH35 in an embodiment of the present invention).
Figure 5:
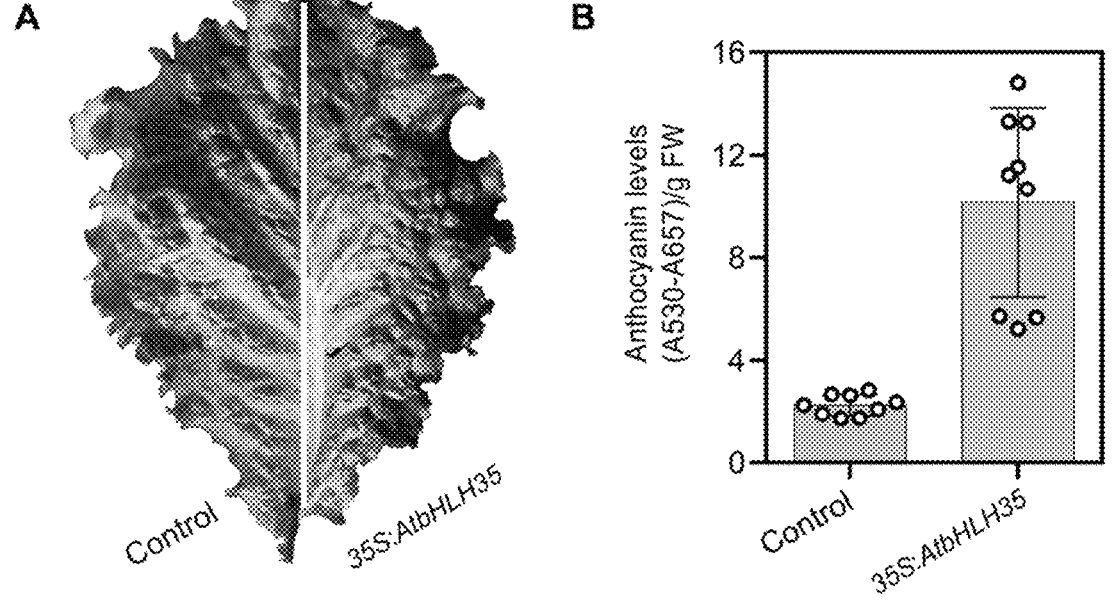
FIG. 5 shows an overexpression phenotype (A) and anthocyanin accumulation content determination (B) of *Lactuca sativa* var. *ramosa* Hort. (overexpressed AtbHLH35 in an embodiment of the present invention).

In order to make the technical solutions of the present invention better understood, the technical solutions of the present invention will be described in further detail below with reference to the embodiments of the present invention and the accompanying drawings. Apparently, the described embodiments are merely some rather than all embodiments of the present invention. Based on the embodiments in the present invention, all other embodiments obtained by those of ordinary skill in the art without making creative labor fall within the scope of protection of the present invention.

It should be noted that the embodiments of the present invention and the features in the embodiments can be combined with each other in case of no conflict. The present invention will be described in detail with reference to embodiments.

An embodiment of the present invention provides an application of the bHLH35 genes of *Corydalis hemidicentra* (ChbHLH35), *Arabidopsis thaliana* (AtbHLH35) and orthologous genes from other angiosperms in breeding of transgenic plants with a high anthocyanin content and breeding of transgenic plants with tolerance to an abiotic stress environment.

In the present invention, experimental materials used in the following examples are *Corydalis hemidicentra, Lactuca sativa* var. *ramosa* Hort. and *Arabidopsis thaliana* (Col-0) (*Arabidopsis* Biological Resource Center, Stock No. CS28166).

Example 1 Cloning of bHLH35 Sequence for Promoting Anthocyanin Accumulation

Total RNA of mature leaves of *Corydalis hemidicentra* and *Arabidopsis thaliana* was extracted by SteadyPure plant RNA extraction kit (AG21019, Wuhan). About 0.5 g of leaf tissue was promptly frozen in liquid nitrogen and ground into powder. The high-purity RNA with the genome removed was obtained according to instructions of the kit, its concentration was determined and then high-purity RNA was stored in a refrigerator at −80° C. for future use. For cDNA synthesis, 1 µg of the total RNA was utilized with the Evo M-MLV Plus cDNA synthesis kit (AG11615, Wuhan). The synthesized cDNA served as a template for cloning the bHLH35 genes.

A full-length sequence of AtbHLH35 was downloaded from The *Arabidopsis* Information Resource database and the sequences of ChbHLH35 was obtained from the assembled genome of *Corydalis hemidicentra* in this experiment. The cloning primers as follows were designed:

```
AtbHLH35-F (XbaI):
TCT AGA ATGGAGGATATCGTCGACCA

AtbHLH35-R (KpnI):
GGT ACC TTAACCGCAACACCTCTTGTTCT

ChbHLH35-F (XbaI):
TCT AGA ATGGAACACATTGATGAAGACT

ChbHLH35-R (KpnI):
GGT ACC TTAGTAAATTACCTCGACAAAGACAGTCT
```

Where underlined, sequences are restriction endonuclease site sequences used for cloning.

By using a high-fidelity ApexHF HS DNA polymerase (AG12201, Wuhan) and the synthetized cDNA template, a target segment was amplified and recovered according to a procedure (which was set as 98° C. for 10 s, 55° C. for 5 s and 72° C. for 1 min, and circulated for 32 times). The purified segment was ligated into a pCE3 vector using the Ultra-universal TOPO Cloning Kit (C603-01, Vazyme, Nanjing) and subsequent sequencing was performed. Through comparison with the reference sequence, the correctly cloned vector was subjected to double enzyme digestion using XbaI and KpnI (NEB, UK). Simultaneously, pCAMBIA1300 was also digested with the same restriction endonuclease. After recovering the target segment, the bHLH35 segment was ligated into the plant expression vector pCAMBIA1300 using T4 DNA ligase (NEB, UK). The ChbHLH35 CDS sequence by sequencing had a length of 663 nucleotides from the initiation codon to the termination codon, and its nucleotide sequence is shown in SEQ ID No. 1, while the corresponding amino acid sequence is shown in SEQ ID No. 2. The nucleotide sequence of AtbHLH35 is consistent with a reference sequence (NM_001203627), as shown in SEQ ID No: 3, and a protein sequence is F4KAJ5, as shown in SEQ ID No: 4.

Example 2 Acquisition of ChbHLH35 and AtbHLH35 Transgenic Plants pCAMBIA1300-ChbHLH35 and pCAMBIA1300-AtbHLH35 were transferred into *agrobacterium* GV3101 and positive clones were screened on a YEP agar plate containing 10 mg/L rifampicin and 50 mg/L kanamycin. After PCR verification, correct clones were subjected to shaking culture. For the transformation of *Arabidopsis thaliana*, the flower dipping method was employed. *Lactuca sativa* var. *ramosa* Hort. was infected by using a leaf disc method to generate transgenic plants and the positive transgenic plants were selected using 25 mg/L hygromycin.

Example 3 Detection of Expression Levels of Anthocyanin Biosynthesis-Related Genes in ChbHLH35 and AtbHLH35 Transgenic *Arabidopsis thaliana*

Two independent ChbHLH35 and AtbHLH35 transgenic *Arabidopsis thaliana* lines were selected and subjected to high light treatment for inducing anthocyanin accumulation, and the untreated lines were used as a control group. About 0.5 g of mature leaves were collected and subjected to RNA extraction using the method described in Example 1. The relative expression levels of genes (CHS, CHI, F3H, DFR, ANS, UFGT) involved in anthocyanin biosynthesis were detected by qRT-PCR. It was found that the expression of these anthocyanin biosynthesis-related genes in both ChbHLH35 and AtbHLH35 transgenic lines was significantly upregulated compared to the wild type, regardless of whether the plants were subjected to high light treatment or not.

Example 4 Determination of Anthocyanin Content in ChbHLH35 and AtbHLH35 Transgenic Plants Approximately 0.1 g mature leaves of transgenic *Arabidopsis thaliana* and *Lactuca sativa* var. *ramosa* Hort. were collected with or without high light treatment. The leaves were rapidly frozen in liquid nitrogen and ground into powder. A mixture of 1 mL of hydrochloric acid:methanol (1:99) solution was added into the powder, and placed in the dark at 4° C. overnight to extract the anthocyanins. A light absorption value of an extract was measured at 530 nm and 657 nm, and the anthocyanin content was calculated by the formula: (A530 value−0.25×A657 value)/fresh weight (unit/mg). The calculation results demonstrated that the anthocyanin content in both ChbHLH35 and AtbHLH35 transgenic *Arabidopsis thaliana*, as well as in AtbHLH35 transgenic *Lactuca sativa* var. *ramosa* Hort. were significantly higher than those in the control group. Furthermore, it was observed that high light treatment induced more anthocyanin accumulation in the transgenic *Arabidopsis thaliana* plants.

In summary, the ChbHLH35 gene from *Corydalis hemidicentra* and the AtbHLH35 gene from *Arabidopsis thaliana* in the present invention, are key genes in angiosperms for regulating the biosynthesis of anthocyanin. Both bHLH35 genes effectively activate the expression of genes involved in anthocyanin biosynthesis, leading to a significant increase in anthocyanin content in transgenic plants. The discovery of these genes holds significant theoretical and practical importance in the cultivation of agricultural products with insect resistance, antioxidation and anti-aging effects.

The above specific examples are only an explanation of the present invention, rather than a limitation of the present invention. After reading this description, those skilled in the art may make modifications as required without inventive contribution to the present examples, but they are protected by the patent law as long as they are within the scope of the claims of the present invention.

---

What is claimed is:

1. A method for cultivating transgenic plants having increased anthocyanin content, comprising the following step: transferring a bHLH35 gene into recipient plants using a genetic engineering transformation method, to obtain transgenic plants having increased anthocyanin content; wherein the bHLH35 gene is selected from the group consisting of: a ChbHLH35 gene from *Corydalis hemidi-centra*, wherein the nucleotide sequence of the ChbHLH35 gene is shown in SEQ ID No: 1, and the amino acid sequence encoded by the ChbHLH35 gene is shown in SEQ ID No: 2; or an AtbHLH35 gene from *Arabidopsis thaliana* wherein the nucleotide sequence of the AtbHLH35 gene is shown in SEQ ID No: 3, and the amino acid sequence encoded by the AtbHLH35 gene is shown in SEQ ID No: 4.

* * * * *

SEQUENCE LISTING

```
Sequence total quantity: 4
SEQ ID NO: 1          moltype = DNA  length = 663
FEATURE               Location/Qualifiers
source                1..663
                      mol_type = other DNA
                      organism = synthetic construct
SEQUENCE: 1
atggaacaca ttgatgaaga ctacaaacat tactgggaaa caaaaatgtt ttttcaaaat   60
gaagaactcg acagtttggt ttacgacgag caaatttccg gttacgacga gcaagtttcg  120
ggttactatg attcgagctc tccggacgct tcatcggtca cagcgaaaaa tataatttca  180
gaaagaaata ggaggaaaaa acttaatgat agattatttg cattaagagc tgtggttcct  240
aatattagca agatggataa agcatcgata attaaggacg cgatcgagta catccaagaa  300
ttacacgaac aagaacgagc aatccaagta gagttaattg agctcgaatc ggggaaattg  360
aagaaaccca tgttggatat cgaacgacaa aatgcaggtt tattgaagac gaagaaaaag  420
agaatagata ctaattatga ttcgagtgga tcgagatcgt catcgatcga attgctagag  480
cttagagttt cgtacgtggg agatagaact atggtggtaa gtctcacgtg cgataaaaaa  540
acagacacaa tggtgaagct ctgtgaagtt ttcgagtctt tgaagcttaa aatagtcact  600
gcaagtatca ctgtttctc agggagactt ctcaagactg tctttgtcga ggtaatttac  660
taa                                                               663

SEQ ID NO: 2          moltype = AA  length = 220
FEATURE               Location/Qualifiers
source                1..220
                      mol_type = protein
                      organism = synthetic construct
SEQUENCE: 2
MEHIDEDYKH YWETKMFFQN EELDSLVYDE QISGYDEQVS GYYDSSSPDA SSVTAKNIIS   60
ERNRRKKLND RLFALRAVVP NISKMDKASI IKDAIEYIQE LHEQERAIQV ELIELESGKL  120
```

-continued

```
KKPMLDIERQ NAGLLKTKKK RIDTNYDSSG SRSSSIELLE LRVSYVGDRT MVVSLTCDKK  180
TDTMVKLCEV FESLKLKIVT ASITVFSGRL LKTVFVEVIY                        220

SEQ ID NO: 3              moltype = DNA  length = 795
FEATURE                   Location/Qualifiers
source                    1..795
                          mol_type = other DNA
                          organism = synthetic construct
SEQUENCE: 3
atggaggata tcgtcgacca agaattaagc aattactggg aacctagctc cttcctccaa   60
aacgaagact tcgaatacga cagaagctgg cctttggaag aagccatttc tgggtcgtat  120
gattcgagtt cgccggatgg agctgcttcg tcgccggctt ctaagaatat tgtgtcggag  180
agaaacagaa gacagaaact taaccagaga ctcttcgctc ttcgatcagt tgttcccaat  240
atcactaaga tggataaagc ctcaataatc aaagatgcta ttagttacat agaaggatta  300
caatatgaag aaaagaagct cgaagctgag atcagagaac ttgaatctac accaaagagt  360
agccttagtt tcagcaaaga ttttgatcgt gatttacttg ttcctgtcac atccaagaag  420
atgaagcagc ttgattctgg ttcttccact tctctcatcg aagttctcga attgaaggta  480
acattcatgg gagagaggac aatggtggtg agtgtaacat gtaataagag gacagataca  540
atggtgaaac tgtgtgaagt ctttgagtca ttgaatctca aaatcctcac ttccaatctc  600
acctctttct ctggcatgat cttccacact gtctttattg agttgcgacc aaacatttat  660
tgggttgtgt ggttttttagt ttttatgtct atttttggtc ccacaattat tgtaatttgg  720
tccatttggt ttattaaaaa gaaaataata ttatctctgt ggcggatgaa gaagaacaag  780
aggtgttgcg gttaa                                                   795

SEQ ID NO: 4              moltype = AA  length = 264
FEATURE                   Location/Qualifiers
source                    1..264
                          mol_type = protein
                          organism = synthetic construct
SEQUENCE: 4
MEDIVDQELS NYWEPSSFLQ NEDFEYDRSW PLEEAISGSY DSSSPDGAAS SPASKNIVSE   60
RNRRQKLNQR LFALRSVVPN ITKMDKASII KDAISYIEGL QYEEKKLEAE IRELESTPKS  120
SLSFSKDFDR DLLVPVTSKK MKQLDSGSST SLIEVLELKV TFMGERTMVV SVTCNKRTDT  180
MVKLCEVFES LNLKILTSNL TSFSGMIFHT VFIELRPNIY WVVWFLVFMS IFGPTIIVIW  240
SIWFIKKKII LSLWRMKKNK RCCG                                         264
```